(12) United States Patent  (10) Patent No.: US 8,548,599 B2
Zarsky et al.  (45) Date of Patent: *Oct. 1, 2013

(54) METHODS AND SYSTEMS FOR SUBCUTANEOUS TREATMENTS

(75) Inventors: Jan Zarsky, Framingham, MA (US); Tomáš Schwarz, Prague (CZ)

(73) Assignee: BTL Holdings Limited, Limassol (CY)

( * ) Notice: Subject to any disclaimer, the term of this patent is extended or adjusted under 35 U.S.C. 154(b) by 7 days.

This patent is subject to a terminal disclaimer.

(21) Appl. No.: 13/297,608

(22) Filed: Nov. 16, 2011

(65) Prior Publication Data

US 2013/0123764 A1  May 16, 2013

(51) Int. Cl.
 *A61N 5/02* (2006.01)
(52) U.S. Cl.
 USPC .......................................... 607/101; 607/102
(58) Field of Classification Search
 USPC .................................. 607/101, 102
 See application file for complete search history.

(56) References Cited

U.S. PATENT DOCUMENTS

| 5,660,836 | A | 8/1997 | Knowlton | |
|---|---|---|---|---|
| 5,755,753 | A | 5/1998 | Knowlton | |
| 5,919,219 | A | 7/1999 | Knowlton | |
| 6,047,215 | A * | 4/2000 | McClure et al. | 607/101 |
| 6,241,753 | B1 | 6/2001 | Knowlton | |
| 6,334,074 | B1 * | 12/2001 | Spertell | 607/101 |
| 6,377,855 | B1 | 4/2002 | Knowlton | |
| 6,381,498 | B1 | 4/2002 | Knowlton | |
| 6,387,380 | B1 | 5/2002 | Knowlton | |
| 6,405,090 | B1 | 6/2002 | Knowlton | |
| 6,406,474 | B1 | 6/2002 | Neuberger et al. | |
| 6,413,255 | B1 * | 7/2002 | Stern | 606/41 |
| 6,511,475 | B1 | 1/2003 | Altshuler et al. | |
| 6,662,054 | B2 * | 12/2003 | Kreindel et al. | 607/101 |
| 6,725,095 | B2 * | 4/2004 | Fenn et al. | 607/101 |
| 6,749,624 | B2 | 6/2004 | Knowlton | |
| 6,766,202 | B2 * | 7/2004 | Underwood et al. | 607/99 |
| 7,006,874 | B2 | 2/2006 | Knowlton et al. | |
| 7,189,230 | B2 | 3/2007 | Knowlton | |
| 7,229,436 | B2 | 6/2007 | Stern et al. | |
| 7,267,675 | B2 | 9/2007 | Stern et al. | |
| 7,630,774 | B2 * | 12/2009 | Karni et al. | 607/101 |
| 7,643,883 | B2 * | 1/2010 | Kreindel | 607/101 |
| 2003/0187488 | A1 * | 10/2003 | Kreindel et al. | 607/101 |
| 2004/0044385 | A1 * | 3/2004 | Fenn et al. | 607/100 |
| 2005/0182462 | A1 * | 8/2005 | Chornenky et al. | 607/99 |
| 2006/0036300 | A1 * | 2/2006 | Kreindel | 607/99 |
| 2006/0094988 | A1 * | 5/2006 | Tosaya et al. | 601/2 |
| 2006/0173518 | A1 * | 8/2006 | Kreindel | 607/101 |
| 2006/0265034 | A1 * | 11/2006 | Aknine et al. | 607/101 |
| 2007/0038206 | A1 * | 2/2007 | Altshuler et al. | 606/20 |
| 2007/0106349 | A1 * | 5/2007 | Karni et al. | 607/101 |
| 2007/0282318 | A1 * | 12/2007 | Spooner et al. | 606/32 |
| 2008/0009885 | A1 * | 1/2008 | Del Giglio | 606/128 |
| 2008/0183167 | A1 * | 7/2008 | Britva et al. | 606/41 |

(Continued)

*Primary Examiner* — Linda Dvorak
*Assistant Examiner* — Kaitlyn Smith
(74) *Attorney, Agent, or Firm* — Kenneth H. Ohriner; Perkins Coie LLP

(57) ABSTRACT

Methods for focused remodeling and downsizing the volume of subcutaneous lipid-rich cells, body contouring, and tightening skin tissue, using controlled heating of the targeted areas on the body. The electromagnetic energy heats the subcutaneous tissues which provides the desired effect. The electromagnetic energy is applied via an applicator without touching the skin. A spacer of insulating or dielectric material may be provided between the applicator and the skin.

10 Claims, 2 Drawing Sheets

(56) References Cited

U.S. PATENT DOCUMENTS

| | | | |
|---|---|---|---|
| 2008/0183251 A1* | 7/2008 | Azar et al. | 607/101 |
| 2009/0024193 A1* | 1/2009 | Altshuler et al. | 607/100 |
| 2009/0125013 A1* | 5/2009 | Sypniewski et al. | 606/33 |
| 2009/0221938 A1* | 9/2009 | Rosenberg et al. | 601/2 |
| 2010/0100092 A1* | 4/2010 | Turner et al. | 606/33 |
| 2010/0286673 A1* | 11/2010 | Altshuler et al. | 606/9 |
| 2011/0112520 A1* | 5/2011 | Michael | 606/13 |
| 2011/0295187 A1* | 12/2011 | Shanks et al. | 604/20 |
| 2012/0010609 A1* | 1/2012 | Deem et al. | 606/33 |
| 2012/0022622 A1* | 1/2012 | Johnson et al. | 607/101 |
| 2012/0078141 A1* | 3/2012 | Knowlton | 601/3 |
| 2013/0123629 A1* | 5/2013 | Rosenberg et al. | 600/442 |

* cited by examiner

METHODS AND SYSTEMS FOR SUBCUTANEOUS TREATMENTS

FIELD OF THE INVENTION

The field of the invention is non-invasive, non-traumatic focused remodeling and downsizing subcutaneous lipid-rich cells, body contouring and skin tightening. In particular, the invention relates to controlled heating of the targeted areas on the human body using electromagnetic waves without direct contact with the skin.

BACKGROUND OF THE INVENTION

Human skin is composed of three basic elements: the epidermis, the dermis and the hypodermis or so called subcutis. The dermis consists of collagen, elastic tissue and reticular fibers. The hypodermis is the lowest layer of skin and contains hair follicle roots, lymphatic vessels, collagen tissue, nerves and also subcutaneous fat forming an adipose fat tissue. Adipose fat tissue is formed by aggregation of fat cells containing stored lipid (fat). Most fat tissue accumulations result from lipids (fat) primarily from food, when energy intake derived from food exceeds daily energy needs. This may result in an increase in fat cell size or fat cell number or both. Mature fat cells are very large, ranging up to 120 microns in diameter and containing as much as 95% lipid (fat) by volume. The subcutaneous adipose tissue layer may be thin (about 1 cm or less) or in humans of slight or moderate body type.

Excess adipose tissue may be perceived as aesthetically undesirable. Dieting and exercise may result in reduction of adipose tissue and weight loss. However, for most people, the reduction in adipose tissue volume occurs rather unpredictably from all anatomical areas. This can leave the areas intended for reduction, for example, the abdomen, largely unaffected, even after significant body weight loss. Various invasive and non-invasive methods have been developed to remove unwanted subcutaneous fat from specific areas of the body.

The main invasive method is surgical-assisted liposuction, where selected volumes of subcutaneous fat are mechanically aspirated out from the patient at desired anatomical sites of the body. However, liposuction procedures are invasive and can be painful and traumatic, with many undesirable side effects and risks. Lipodissolve is another invasive procedure involving a series of drug injections intended to dissolve and permanently remove small pockets of fat from various parts of the body. It also is known as mesotherapy, lipozap, lipotherapy, or injection lipolysis. Lipodissolve also has many disadvantages and risks, to the extent that various medical associations have issued health warnings against using it.

The non-invasive methods concentrate on the acceleration of the lipolysis as the natural process of the fat reduction. This can be achieved in several ways. One of them is application of pharmaceuticals accelerating the lipolysis. However, when applied topically they tend only to affect the outermost layers of the skin, rarely penetrating to the subdermal vascular plexus. Another method uses radio frequency or ultrasound energy focused on adipose tissue to cause cell destruction and death. These methods tend to damage the melanocyte in the epidermis. The hyperthermic temperatures destroy the target tissues and leave the body to remove the dead cellular and other debris. Non-invasive heating techniques have also been used. These involve heating the adipose fat tissue to about 40° C. or more via direct contact with a heating element. These non-invasive methods have certain disadvantages as well, and have been used with varying degrees of success.

Accordingly, there is need for improved methods and systems for subcutaneous treatments.

SUMMARY OF THE INVENTION

New methods have now been invented. A method for treating subcutaneous tissue includes positioning one or more applicators adjacent to the skin of a patient, but not touching the skin. Electromagnetic energy is transmitted from the applicators into the subcutaneous tissue. The subcutaneous tissue is heated via the electromagnetic energy. The subcutaneous tissue may be remodeled. The volume of lipid-rich cells in the subcutaneous tissue may be reduced via the heating. The electromagnetic waves may be applied in a pulsed mode or in a continuous mode. The skin may optionally be actively cooled, without contacting the skin. This method may also be used for tightening the skin and for remodeling collagen tissue in the subcutaneous tissue. With the applicator not touching the skin, the need for cooling the skin, and bio-compatibility factors are avoided. There is also a lower risk of over heating the skin, and there is no need to continuously move the applicator.

DETAILED DESCRIPTION

Figure 1:
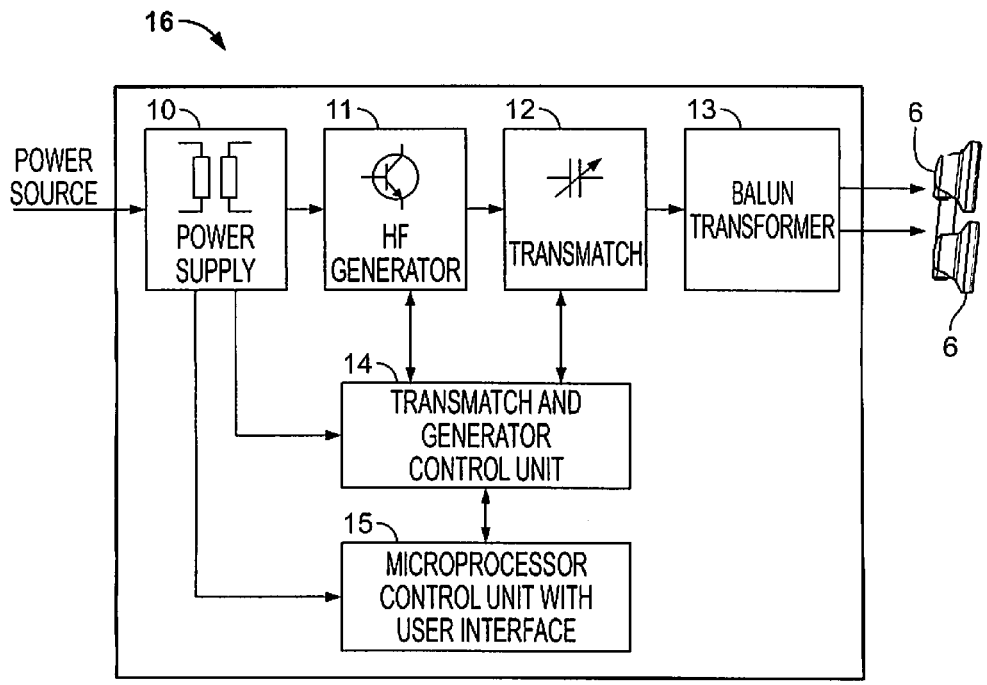
FIG. 1 is a schematic diagram of a system for controlled deep heating of sub dermal tissues.

Methods and apparatus for focused remodeling and downsizing the volume of subcutaneous lipid-rich cells, body contouring and tightening skin tissue, without contact with the skin, have now been invented. Prior art methods generally require direct contact of an applicator onto the skin. This in turn typically also requires use of active skin cooling elements. Direct skin contact can also raise bio-compatibility issues with the applicator material and further requires high sanitary standards, since the applicators are used for treatment of different patients. The practitioner must also be skilled in using the applicators since there is a risk of burning the patient.

These disadvantages are overcome by transmitting electromagnetic energy into the sub subcutaneous tissue, without physical contact with the patient. Contactless application enables simultaneous treatments of large areas of human body. It also avoids the need for artificial cooling of the skin. In the present contactless methods, the skin may be sufficiently cooled passively by circulating air. Optionally, the skin may be cooled via a stream of chilled or room temperature air. The present methods also do not require use of cooling fluids and gels. This reduces costs and increases patient comfort.

In one aspect, the present methods work on the principle of selective deep heating of the human tissue containing low volume of water, such as adipose tissue. Radiant energy may be provided to the sub dermal tissue by one or more capacitive electrodes generating an electromagnetic field. Selective heating in the dermis occurs due to dielectric losses. An inductive electrode may alternatively be used.

In a continuous application mode, the electromagnetic field is applied continuously, which provides a maximum amount of heating. Using a pulse mode, the heat is local and typically limited to about 400 W. With the pulse mode, a high frequency field is applied in short intervals (typically (50-2000 μs) and on various pulse frequencies (typically 50 to 1500 Hz). The maximum output with the continuous method is typically limited to 200 W.

The increase of the temperature in the dermal and the sub dermal tissues also affects the triple-helix structure of collagen fibers contained in such tissues. This may result in remodeling and rejuvenation of collagen, increase of skin density and dermal thickening based on neocollagenesis. Skin tightening may also be achieved.

Remodeling and reducing the volume of subcutaneous lipid-rich cells, and skin tightening in the targeted areas, can change the overall appearance of the body, for use in body contouring and body reshaping.

Electromagnetic energy is provided through the skin to the underlying sub dermal tissue, without contacting the skin. The radiant energy is converted into heat in the sub dermal tissue. The radiant energy enables focused heating of the subcutaneous adipose tissue and sub dermal collagen tissue, leading to accelerating lipolysis. At the same time the triple-helix structure of collagen fibers may result in remodeling and/or rejuvenation of collagen, increase of skin density and dermal thickening based on neocollagenesis. Subcutaneous lipid-rich cells may be remodeled and/or reduced in volume, contouring and tightening skin tissue.

Referring now to FIG. 1, a system 16 applies electromagnetic energy through a skin layer, such as the epidermis, and to the underlying sub dermal tissue, and underlying collagen tissue, causing acceleration of lipolysis and collagen remodeling. The system may include 6 blocks. The power supply 10 is connected to a power source. An HF generator (high frequency generator) 11 and a transmatch and generator control unit 14, and a microprocessor control unit with user interface 15, are connected to the power supply 10. The HF generator 11 may generate an electromagnetic field at 13.56 or 40.68 or 27.12 MHz, or 2.45 GHz or optionally at other frequencies as well. The 13.56, 27.12 and 40.68 MHz and 2.45 GHz frequencies avoid creating radio interference, as these frequencies are exclusively assigned as free or open frequencies.

The microprocessor control unit with user interface 15 provides communication between the transmatch and generator control unit 14 and user interface, which may be a touch screen on the device display.

The transmatch and generator control unit 14 receives information from the operator via the control unit and regulates the operation of the HF generator 11 and the transmatch 12. The transmatch transmits HF to a balun transformer 13, which converts unbalanced impedance to balanced impedance. This processed signal goes to two capacitive applicators 6, which may be positioned approximately 2-3 cm above the surface of the skin or applied on dielectric material which is in contact with the skin surface.

Figure 2:
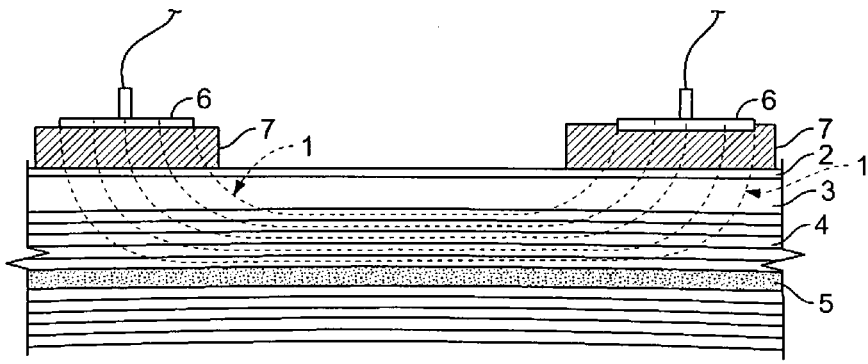
FIG. 2 is a schematic view of a trans-regional course of electromagnetic field.

FIG. 2 is a schematic representation of a heat distribution under the skin. One or more applicators 6 create an electromagnetic field. This electromagnetic field crosses through the skin 2, subcutaneous fat 3 and muscle 4 or the bone 5. Capacitive applicators 6 provide deep heating, which heats selectively only structures with low volume, of water. A spacer 7 such as a towel, gauze pad, foam pad, cloth pad, etc. may be placed on the skin, with the applicator then placed on top of the spacer 7. This automatically sets the separation distance between the applicator and the skin, and prevents the applicator from touching the skin. The spacer 7 may be made of various dielectric or electrically non-conductive materials. The spacer 7 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

A selective heating process is observed in the dermis 3 due to dielectric losses. Dielectric loss is created, as part of an AC electromagnetic field power is converted to heat in the dielectric. During this process, polar molecules rotate, and their movement produces the thermal energy. Skin and muscle, are largely not affected by electromagnetic field 1 as they contain water and the blood, circulation provides for cooling. Bone 5 gets little if any heating because the applicators 6 are positioned to create a field only on the upper structures. The lipid cells of the adipose tissue contain less water than the surrounding tissue and are therefore heated at higher level than the surrounding tissue.

Figure 3:
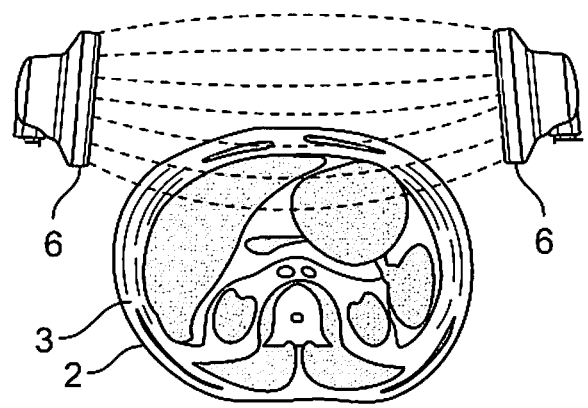
FIGS. 3 and 4 are schematic examples of positioning of electrodes shown in FIG. 1.
Figure 4:
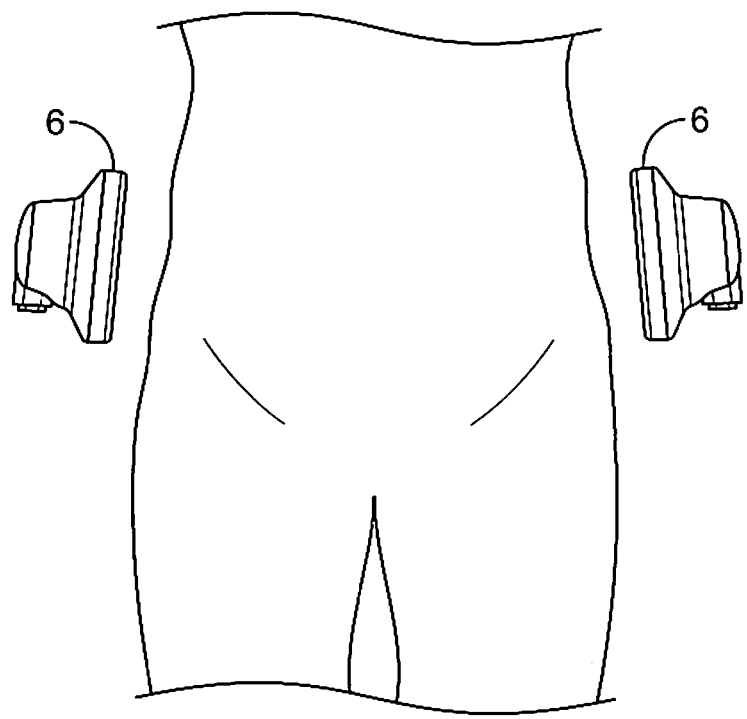

FIGS. 3 and 4 are schematic examples of positioning of the applicators or electrodes 6 providing radiant energy through the skin 2 to subcutaneous fat 3. The electrodes are positioned approximately 2-3 cm above the surface of the skin and separated from the skin by an air gap, or placed onto a spacer 7 which is in contact with the skin surface, as shown in FIG. 5. The spacer 7, if used, may correspondingly typically be about 0.5 to 1 cm thick. The applicator 6 may be temporarily fixed in position relative to the patient, if desired, for example on a mechanical fixture or holder. It is not necessary in each instance for the applicator to be continuously moving during the procedure. This makes the procedure easier to perform, since user need not constantly keep moving the applicator over the patient's skin. Consequently, the user can accordingly simultaneously attend to other needs of a patient. The applicator 6 may have a relatively large surface area, so that the field 1 is distributed more widely through the subcutaneous tissue. For example, the applicator may have a surface area of at least about 15, 30, 50, 100, or 150 $cm^2$.

If more than one applicator is used, applicators may be positioned on opposite sides of the patient. A spacer may be positioned between one or more applicator and the skin of the patient. The electromagnetic waves may be transmitted in the range of 13.553-13.567 or 26.957-27.283 or 40.66-40.70 MHz or 2.4-2.5 GHz from the applicator into the subcutaneous tissue. The temperature of the skin surface may be increased to about 32-45° C.

Thus, novel methods and systems have been shown and described. Various modifications and substitutions may be made without departing from the spirit and scope of the invention. The invention, therefore, should not be limited, except by the following claims and their equivalents.

What is claimed is:

1. A method for treating subcutaneous tissue of a patient having a volume of lipid-rich cells, comprising:
    positioning an applicator having a surface area of at least 15 $cm^2$ adjacent to the skin of the patient, with the applicator spaced apart from the skin of the patient, with the applicator not directly or indirectly in contact with the skin of the patient, and with the applicator separated from the skin by an air gap;
    transmitting radio frequency waves from the applicator into the subcutaneous tissue;
    heating the subcutaneous tissue via radio frequency waves without cooling the skin of the patient; and
    remodeling and/or downsizing the volume of lipid-rich cells in the subcutaneous tissue via the heating.

2. The method of claim 1 further comprising spacing the applicator 2-3 cm away from the skin of the patient.

3. The method of claim 2 further comprising applying the radio frequency waves with pulse width between 50-2000 micro seconds and pulse frequency range from 50-1500 Hz.

4. The method of claim 1 further comprising applying radio frequency waves in a pulsed mode with a power range of 30-400 W per pulse.

5. The method of claim 1 further comprising applying the radio frequency waves in a continuous mode.

6. The method of claim 1 wherein the temperature of skin is increased to about 32-45° C. while treating the subcutaneous tissue.

7. The method of claim 1 further comprising positioning a second applicator adjacent to the skin of the patient, with the applicators not touching the skin of the patient, and with the applicators comprising capacitive electrodes.

8. The method of claim 1 wherein the applicator comprises an inductive electrode.

9. The method of claim 1 further comprising transmitting radio frequency waves in the range of 13.553-13.567 or 26,957-27,283 or 40.66-40.70 MHz or 2.4-2.5 GHz from the applicator into the subcutaneous tissue.

10. A method for treating subcutaneous tissue of a patient having a volume of lipid-rich cells, comprising:
   positioning an applicator adjacent to the skin of the patient, with the applicator separated from the skin by an air gap;
   transmitting radio frequency waves from the applicator into the subcutaneous tissue;
   heating the subcutaneous tissue via radio frequency waves without cooling the skin of the patient; and
   remodeling and/or downsizing the volume of lipid-rich cells in the subcutaneous tissue via the heating.

* * * * *